United States Patent
Angelo et al.

(10) Patent No.: US 9,958,442 B2
(45) Date of Patent: *May 1, 2018

(54) SENSORS INCORPORATING ANTIBODIES AND METHODS OF MAKING AND USING THE SAME

(75) Inventors: R. Michael Angelo, Berkeley, CA (US); April S. Brown, Hillsborough, NC (US); Scott Wolter, Hillsborough, NC (US); William V. Lampert, Raleigh, NC (US)

(73) Assignee: Duke University, Durham, NC (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 13/201,181

(22) PCT Filed: Feb. 11, 2010

(86) PCT No.: PCT/US2010/023917
§ 371 (c)(1),
(2), (4) Date: Aug. 11, 2011

(87) PCT Pub. No.: WO2010/096331
PCT Pub. Date: Aug. 26, 2010

(65) Prior Publication Data
US 2012/0122736 A1    May 17, 2012

Related U.S. Application Data

(60) Provisional application No. 61/151,761, filed on Feb. 11, 2009.

(51) Int. Cl.
*G01N 33/53* (2006.01)
*G01N 33/543* (2006.01)

(52) U.S. Cl.
CPC .......... *G01N 33/5438* (2013.01); *Y10T 29/41* (2015.01)

(58) Field of Classification Search
None
See application file for complete search history.

(56) References Cited

U.S. PATENT DOCUMENTS

| | | |
|---|---|---|
| 5,567,301 A | 10/1996 | Stetter et al. |
| 5,603,820 A | 2/1997 | Malinski et al. |
| 5,674,700 A * | 10/1997 | Maurel .......................... 435/7.94 |
| 6,144,040 A | 11/2000 | Ashton |
| 6,329,209 B1 | 12/2001 | Wagner et al. |
| 6,365,418 B1 | 4/2002 | Wagner et al. |
| 6,433,356 B1 | 8/2002 | Cahen et al. |
| 6,647,796 B2 | 11/2003 | Beach et al. |
| 6,682,942 B1 | 1/2004 | Wagner et al. |
| 6,716,620 B2 | 4/2004 | Bashir et al. |
| 6,780,582 B1 | 8/2004 | Wagner et al. |
| 6,896,872 B2 | 5/2005 | Dambinova |
| 6,897,073 B2 | 5/2005 | Wagner et al. |
| 7,144,705 B2 | 12/2006 | Hochstrasser et al. |
| 7,247,469 B2 | 7/2007 | Wagner et al. |
| 7,341,692 B2 | 3/2008 | Willett et al. |
| 7,361,946 B2 | 4/2008 | Johnson et al. |
| 7,427,490 B2 | 9/2008 | Valkirs et al. |
| 7,504,658 B2 | 3/2009 | Kunze et al. |
| 7,868,354 B2 | 1/2011 | Garcia et al. |
| 8,828,713 B2 * | 9/2014 | Ren ..................... G01N 27/4145 422/68.1 |
| 2003/0036054 A1 * | 2/2003 | Ladisch et al. .................... 435/5 |
| 2003/0059954 A1 * | 3/2003 | Vikholm .......... G01N 33/54373 436/518 |
| 2003/0096331 A1 | 5/2003 | Dambinova |
| 2003/0138829 A1 * | 7/2003 | Unger et al. ...................... 435/6 |
| 2003/0148404 A1 | 8/2003 | Michaelson |
| 2003/0197503 A1 | 10/2003 | Kawano et al. |
| 2003/0199000 A1 | 10/2003 | Valkirs et al. |
| 2004/0072360 A1 | 4/2004 | Naaman et al. |
| 2004/0115711 A1 | 6/2004 | Su et al. |
| 2004/0157281 A1 * | 8/2004 | Hulkower et al. ........... 435/7.92 |
| 2004/0159836 A1 | 8/2004 | Sugimoto et al. |
| 2005/0097941 A1 | 5/2005 | Sandvik et al. |
| 2006/0046259 A1 | 3/2006 | Baird et al. |

(Continued)

FOREIGN PATENT DOCUMENTS

| | | |
|---|---|---|
| EP | 1801886 | 6/2007 |
| EP | 2019318 | 1/2009 |

(Continued)

OTHER PUBLICATIONS

International Search Report and Written Opinion for Application No. PCT/US2010/023917 dated Jun. 14, 2010 (17 pages).
Allard, L. et al., "Park7 and nucleoside diphosphate kinase as a plasma markers for the early diagnosis of stroke," Clin. Chem. (2005) 51:2043-2051.
Castillo, J. et al., "The release of tumor necrosis factor-alpha is associated with ischemic tolerance in human stroke," Ann. Neurol. (2003) 54:811-819.
Dahlen, J., "A novel panel of markers to diagnose stroke," Proceedings of the 10th Asian Pacific Congress of Clinical Biochemistry in conjunction with the Australasian Association of Clinical Biochemists' 42 Annual Scientific Conference, published in Clinical Biochem. Rev. (2004) 25(Suppl):S18-S128.

(Continued)

*Primary Examiner* — Changhwa J Cheu
(74) *Attorney, Agent, or Firm* — Michael Best & Friedrich LLP

(57) ABSTRACT

A sensor comprising an electronic circuit electrically coupled to a type III-V semiconductor material, for example indium arsenide (InAs) and an antibody contacting the type III-V semiconductor material. The sensor produces measurable N changes in the electrical properties of the semiconductor upon antibody-antigen binding events. Electrical properties measurable by the electronic device may include resistivity, capacitance, impedance, and inductance. A method of detecting an antigen using sensors of the invention. A method of detecting a reaction of an analyte to a stimulus using sensors of the invention. Sensor arrays comprising multiple sensors of the invention.

16 Claims, 13 Drawing Sheets

(56) References Cited

U.S. PATENT DOCUMENTS

| | | | |
|---|---|---|---|
| 2006/0166303 A1 | 7/2006 | Spanuth | |
| 2006/0172341 A1 | 8/2006 | Dambinova | |
| 2006/0172342 A1 | 8/2006 | Dambinova | |
| 2006/0267570 A1* | 11/2006 | Arkin | 324/71.4 |
| 2006/0281135 A1 | 12/2006 | Dambinova | |
| 2007/0264623 A1 | 11/2007 | Wang et al. | |
| 2008/0081326 A1 | 4/2008 | Amano | |
| 2008/0204043 A1 | 8/2008 | Wang et al. | |
| 2009/0057650 A1* | 3/2009 | Lieber | B82Y 10/00 257/24 |
| 2009/0306578 A1 | 12/2009 | Sivan et al. | |
| 2010/0188069 A1 | 7/2010 | Ren et al. | |
| 2011/0068372 A1 | 3/2011 | Ren et al. | |
| 2012/0058488 A1 | 3/2012 | Sheppard et al. | |
| 2013/0288378 A1 | 10/2013 | Gu et al. | |

FOREIGN PATENT DOCUMENTS

| | | |
|---|---|---|
| WO | 1993/008464 | 4/1993 |
| WO | 02/048701 | 6/2002 |
| WO | 03/102546 | 12/2003 |
| WO | 2005/124345 | 12/2005 |
| WO | 2007015113 | 2/2007 |
| WO | 2007/092909 | 8/2007 |
| WO | 2007114947 | 10/2007 |
| WO | 2007124439 | 11/2007 |
| WO | 2008008349 | 1/2008 |
| WO | 2008008846 | 1/2008 |
| WO | 2008/105824 | 9/2008 |
| WO | 2010/005738 | 1/2010 |
| WO | 2010096331 | 8/2010 |
| WO | 2015/046858 | 4/2011 |
| WO | 2013/039819 | 3/2013 |

OTHER PUBLICATIONS

Dambinova, S.A. et al., "Multiple panel of biomarkers for tia/stroke evaluation," Stroke (2002) 33:1181-1182.
Freed, M. et al., "Real time in-situ data acquisition using autonomous on-wafer sensor arrays," in ISSM (2000) Tokyo, Japan.
Garcia, M. et al., "Functionalization and characterization of InAs and InP surfaces with hemin," J. Vac. Sci. Technol. (2007) 25:1504-1510.
Jauch, E.C. et al., "Can d-dimer levels identify patients at risk for early neurological deterioration in acute ischemic stroke?" Nature Clin. Pract. Neurol. (2006) 2:590-591.
Katzan, I.L. et al., "Utilization of intravenous tissue plasminogen activator for acute ischemic stroke," Arch. Neurol. (2004) 61:346-350.
Kim, J.S. et al., "Serial measurement of interleukin-6, transforming growth factor-beta, and s-100 protein in patients with acute stroke," Stroke (1996) 27:1553-1557.
Kumar, K., "Overview: use of biomarkers for early diagnosis of ischemic stroke," Curr. Opin. Invest. Drugs (2005) 6:21-24.
Laskowitz, D.T. et al., "Clinical usefulness of a biomarker-based diagnostic test for acute stroke: the biomarker rapid assessment in ischemic injury (brain) study," Stroke (2009) 40:77-85.
Laskowitz, D.T. et al., "Serum markers of cerebral ischemia," Journal of Stroke and Cerebrovascular Diseases: the Official Journal of National Stroke Association (1998) 7:234-241.
Lu, H. et al., "High temperature hall effect sensors based on AlGaN/GaN heterojunctions," J. Appl. Phys. (2006) 99:114510-1-114510-4.
McGirt, M.J. et al., "Serum von willebrand factor, mastrix metalloproteinase-9, and vascular endothelial growth factor levels predict the onset of cerebral vasospasm after aneurysmal subarachnoid hemorrhage," Neurosurg. (2002) 51:1128-1134, discussion 1134-1135.
Montaner, J. et al., "Etiologic diagnosis of ischemic stroke subtypes with plasma biomarkers," Stroke (2008) 39:2280-2287.
Montaner, J. et al., "Matrix metalloproteinase-9 pretreatment level predicts intracranial hemorrhagic complications after thrombolysis in human stroke," Circul. (2003) 107:598-603.
Montaner, J., "Stroke biomarkers: can they help us to guide stroke thrombolysis?" Drug News Perspect. (2006) 19:523-532.
Muir, K.W. et al., "C-reactive protein and outcome after ischemic stroke," Stroke (1999) 30:981-985.
Reynolds, M.A. et al., "Early biomarkers of stroke," Clin. Chem. (2003) 49:1733-1739.
Seripa, D. et al., "Relevance of interleukin-1 receptor antagonist intron-2 polymorphism in ischemic stroke," Cerebrovasc. Dis. (2003) 15:276-281.
Squizzato, A. et al., "D-dimer testing in ischemic stroke and cerebral sinus and venous thrombosis," Seminars in Vascular Medicine (2005) 5:379-386.
Taj, F. et al., "Inflammatory biomarkers of stroke," JPMA The Journal of the Pakistan Medical Assoc. (2007) 57:381-382.
Tarkowski, E. et al., "Early intrathecal production of interleukin-6 predicts the size of brain lesion in stroke," Stroke (1995) 26:1393-1398.
Tsui, D.C., "Electron-tunneling studies of a quantized surface accumulation layer," Phys. Rev. B. (1971) 4 (12):4438-4449.
Uhlrich, J. et al., "Interfacial chemistry and energy band line-up of pentacene with the GaN (0001) surface," J. Crys. Grow. (2007) 300:204-211.
Viktorovitch, P. et al., "Electronic Properties of InAs Surface Quantum Wells Grown on InP(100)," Second International Conference, Denver, Colorado (Apr. 23-25, 1990) 148-152.
Wang, D.Z. et al., "Treating acute stroke patients with intravenous tpa. The osf stroke network experience," Stroke (2000) 31:77-81.
Welch, W.J., "Heat shock proteins as biomarkers for stroke and trauma," Am. J. Med. (2001) 111:669-670.
Whiteley, W. et al., "Blood biomarkers in the diagnosis of ischemic stroke: a systematic review," Stroke (2008) 39:2902-2909.
United States Patent Office Action for U.S. Appl. No. 11/937,375 dated Aug. 24, 2009 (7 pages).
United States Patent Office Action for U.S. Appl. No. 11/937,375 dated Apr. 27, 2010 (8 pages).
United States Patent Office Action for U.S. Appl. No. 11/937,375 dated Jun. 17, 2010 (4 pages).
United States Patent Notice of Allowance for U.S. Appl. No. 11/937,375 dated Jul. 9, 2010 (5 pages).
United States Patent Office Action for U.S. Appl. No. 12/948,946 dated Feb. 1, 2012 (7 pages).
International Search Report and Written Opinion for Application No. PCT/US2009/047546 dated Nov. 2, 2009 (10 pages).
Invitation to Pay Additional Fees for Application No. PCT/US2009/047546 dated Jun. 24, 2009 (2 pages).
United States Patent Office Action for U.S. Appl. No. 12/948,946 dated Aug. 27, 2012 (8 pages).
United States Patent Office Action for U.S. Appl. No. 12/999,262 dated Mar. 26, 2015 (9 pages).
Office Action from the United States Patent and Trademark Office for U.S. Appl. No. 12/999,262 dated May 29, 2014 (12 pages).
United States Patent Office Action for U.S. Appl. No. 12/999,262 dated Oct. 28, 2013 (9 pages).
International Search Report and Written Opinion for Application No. PCT/US2015/020406 dated Jan. 14, 2016 (8 pages).
United States Patent Office Final Action for U.S. Appl. No. 12/999,262 dated Sep. 4, 2015 (10 pages).
Zhao, Y. et al., "Thionitroxides, RSNHO: the structure of the SNO moiety in 'S-nitrosohemoglobin' a possible NO reservoir and transporter," J. Am. Chem. Soc. (2006) pp. 1422-1423.
United States Patent Office Notice of Allowance for U.S. Appl. No. 12/999,262 dated Apr. 3, 2017 (9 pages).
United States Patent Office Action for U.S. Appl. No. 12/999,262 dated Nov. 14, 2016 (11 pages).
Addison, A.W. et al., "Hemoglobin: autoreduction and spectroscopy," Biochem. (1986) 25:4104-4113.
Angelo et al., "Interaction of NO with hemoglobin: from microbes to man," Methods Enzym. (2008) 436:125-158.
Ashkenasy, G. et al., "Molecular engineering of semiconductor surfaces and devices," Acc. Chem. Res. (2002) 35:121-128.

(56) References Cited

OTHER PUBLICATIONS

Battut, V. et al., "Gas sensitivity of InP epitaxial thin layers," Sensors and Actuators B (1997) 44:503-506.
Bayer, M. et al., "Theoretical study of electrolyte gate AlGaN/GaN field effect transistors," Appl. Phys. Lett. (2005) 97:033703, 6 pages.
Bedioui, F. et al., "Electrochemical nitric oxide sensors for biological samples—principle, selected examples and applications," Electroanalysis (2003) 15:5-18.
Bell, G.R. et al., "Accumulation layer profiles at InAs polar surfaces," Applied Phys. Lett. (1997) 71:3688-3690.
Cahen, D. et al., "The cooperative molecular field effect," Adv. Funct. Mater. (2005) 15:1571-1578.
Castellanos, M. et al., "Applicability of biomarkers in ischemic stroke," Cerebrovasc. Dis. (2007) 24 Suppl 1:7-15.
Culotta, E. et al., "NO news is good news," Science (1992) 258(5090):1862-1865.
Eickhoff, M. et al., "Electronics and sensors-based on pyroelectric AlGaN/GaN heterostructures; Part B: sensor applications," Phys. Stat. Sol. (2003) 6:1908-1918.
Flechtner, K. et al., "No-induced reversible switching of the electronic interaction between a porphyrin-coordinated cobalt ion and a silver surface," J. Am. Chem. Soc. (2007) 129:12110-12111.
Garcia, M.A. et al., "Comparison of functionalized III-V semiconductor response for nitric oxide," Sensor Letters (2008) 6:627-634.
Garcia, M.A. et al., "Impact of porphyrin functional groups on InAs gas sensors," (Nov. 5, 2007) 21 pages, Retrieved from the Internet: http://nanohub.org/resources/3149/download/2007.07.19-garcia.mcw.pdf.
Gaston, B., "Nitric oxide and thiol groups," Biochim. Biophys. Acta (1999) 1411:323-333.
Gomez, R. et al., "Instrumentation system for in vivo organ studies," IEEE (2001) 1:261-264.
Gow, A.J. et al., "Reactions between nitric oxide and haemoglobin under physiological conditions," Nature (1998) 391:169-173.
Gow, A.J. et al., "The oxyhemoglobin reaction of nitric oxide," Proc. Natl. Acad. Sci. USA (1999) 96:9027-9032.
Haga, Y. et al., "Biomedical microsystems for minimally invasive diagnosis and treatment," Proceedings of IEEE (2004) 92:98-114.
Herold, S. et al., "Mechanistic studies of S-nitrosothiol formation by NO*/O2 and by NO*/methemoglobin," Arch. Biochem. Biophys. (2005) 436:386-396.
Hess, D.T. et al., "Protein s-nitrosylation: purview and parameters," Nat. Rev. Mol. Cell Biol. (2005) 6:150-166.
Jia et al., "S-nitrosohaemoglobin: a dynamic activity of blood involved in vascular control," Nature (1996) 380:221-226.
Kadish, K.M. et al., editors, Applications: Past, Present and Future. The Porphyrin Handbook, Academic Press: San Diego, CA (1999) vol. 6, pp. 240-250 (cover and table of contents only).
Kirchner, C. et al., "Corrosion protection and long-term chemical functionalization of gallium arsenide in an aqueous environment," Adv. Funct. Mat. (2002) 12(4):266-276.
Kruszyna, R. et la., "Nitrite conversion to nitric oxide in red cells and its stabilization as a nitrosylated valency hybrid of hemoglobin," J. Pharm. Exp. Thera. (1987) 241:307-313.
Lantoine, F. et al., "Selective and sensitive electrochemical measurement of nitric-oxide in aqueous-solution—discussion and new results," J. Electroanal. Chem. (1995) 392:85-89.
Luchsinger, B.P. et al., "Assessments of the chemistry and vasodilatory activity of nitrite with hemoglobin under physiologically relevant conditions," J. Inorg. Biochem. (2005) 99:912-921.
Luchsinger, B.P. et al., "Routes to S-nitrosohemoglobin formation with heme redox and preferential reactivity in the beta subunits," Proc. Natl. Acad. Sci. USA (2003) 100:461-566.
McMahon, T.J. et al., "Extrapulmonary effects of inhaled nitrix oxide: role of reversible S-nitrosylation of erythrocytic hemoglobin," Proc. Am. Thorac. Soc. (2006) 3:153-160.
McMahon, T.J. et al., "Nitric oxide in the human respiratory cycle," Nat. Med. (2002) 8:711-717.
Moore, E.G. et al., "Cooperativitiy in the dissociation of nitric oxide from hemoglobin," J. Biol. Chem. (1976) 251:2788-2794.
Pearton, S.J. et al., "GaN-based diodes and transistors for chemical, gas, biological and pressure sensing," J. Phys. Condens. Matter (2004) 16:R961R994.
Potter, W., "Reduction of nitric oxide to nitrous oxide by cobalt porphyrins and corrins," Fuel Proces. Tech. (1994) 40:355-360.
Rovira, C. et al., "Equilibrium geometries and electronic structure of iron-porphyrin complexes: a density functional study," J. Phys. Chem. A. (1997) 101:8914-8925.
Sharma, V.S. et al., "Reaction of nitric oxide with heme proteins and model compounds of hemoglobin," Biochem. (1987) 26:3837-3843.
Sharma, V.S. et al., "The dissociation of NO from nitrosylhemoglobin," J. Biol. Chem. (1978) 253:6467-6472.
Ship, N.J. et al., "Rates of release of nitric oxide from HbSNO and internal electron transfer," Bioorg. Chem. (2003) 31:3-10.
Singel et al., "Chemical physiology of blood flow regulation by red blood cels," Annu. Rev. Physiol. (1997) 67:99-145.
Smith, R.P., "Chemicals reacting with various forms of hemoglobin: biological significance, mechanisms, and determination," J. For. Sci. (1991) 36:662-672.
Stamler et al., Blood flow regulation by S-nitrosohemoglobin in the physiological oxygen gradient, Science (1997) 276:2034-2037.
Steinhoff, G. et al., "pH response for GaN surfaces and its application for pH-sensitive field-effect transistors," Appl. Phys. Lett. (2003) 83(1):177-179.
Stutzmann, M. et al., "GaN-based heterostructures for sensor applications," Dia. Related Matt. (2002) 11:886-891.
Taketa, F. et al., "Chain nonequivalence in binding of nitric oxide to hemoglobin," J. Biol. Chem. (1978) 253:5448-5451.
Talazac, L. et al., "Air quality evaluation by monolithic InP-based resistive sensors," Sensors and Actuators B: Chemical (2001) 76:258-264.
Talazac, L. et al., "Gas sensing properties of pseudo-Schottky diodes on p-type indium phosphide substrates application to O3 and NO2 monitoring in urban ambient air," Sensors and Actuators B: Chemical (2002) 83:149-159.
Vilan, A. et al., "How organic molecules can control electronic devices," Trends in Biotech. (2002) 20:22-29.
Wierzbowska, K. et al., "Studies of gas sensing, electrical and chemical properties of n-Inp epitaxial surfaces," Physica status Solidi(a) (2006) 203(9):2281-2286.
Wolter, S.D. et al., "Porphyrination of III-V compound semiconductor surfaces for detection of exhaled breath indicators of physiological status," Keynote lecture at SMCBS' 2007 International Workshop, See online Journal of SMCBS' 2007 International Workshop, 2 pages.
Wu, D.G. et al., "Direct detection of low-concentration NO in physiological solutions by a new GaAs-based sensor," Chem. Eur. J. (2001) 7(8):1743-1749.

\* cited by examiner

SENSORS INCORPORATING ANTIBODIES AND METHODS OF MAKING AND USING THE SAME

CROSS-REFERENCE TO RELATED APPLICATIONS

This application claims priority to and is a national stage filing under 35 U.S.C. 371 of International Application No. PCT/US2010/023917 filed on Feb. 11, 2010, which claims the benefit of priority to U.S. Provisional Patent Application Ser. No. 61/151,761 filed on Feb. 11, 2009, each of which is incorporated herein by reference in its entirety. This application claims the benefit of priority to U.S. Provisional Patent Application Ser. No. 61/151,761 filed on Feb. 11, 2009.

STATEMENT REGARDING FEDERALLY FUNDED RESEARCH

This invention was made with U.S. government support under grant number 27-001315 awarded by DARPA. The government has certain rights in the invention.

FIELD OF THE INVENTION

The invention relates to electronic sensors capable of detecting chemical and biological species. In particular, the invention relates to the use of antibodies to produce measurable changes in the electronic properties of a semiconductor that is suitably connected to a circuit that enables the detection of specific chemical or biological species. Chemical or biological species bound by antibodies are broadly described as antigens. The resulting sensors are relatively inexpensive to manufacture and offer high specificity to targeted antigens.

BACKGROUND

Antibody proteins play a key role in the identification and/or destruction of agents within an organism. Antibodies have the ability to specifically bind to certain antigens while not binding to other antigens, despite the antigens having similar structures. However, because of the high specificity, it is necessary for most organisms to have the capacity to make thousands of different antibodies, each antibody specific for a particular antigen.

The human body employs several different immunoglobulin classes of antibodies, depending upon the role the antibody plays in the immune response. Each immunoglobulin class may have thousands of particular variations depending upon the antigen to which the antibody responds. Identified classes include IgG, IgA, IgM, IgD, and IgE. IgG is the most prevalent antibody class found in human serum. A structure of an IgG protein is shown in FIG. 1. As with all IgGs, the structure in FIG. 1 has two binding domains ($F_{ab}$) and a central, non-binding domain ($F_c$).

The specific affinity of an IgG antibody for an antigen is a result of amino acid variations in the antigen binding sites at the ends of the $F_{ab}$ fragments. The specific affinity is often described as a "lock and key" mechanism, as is illustrated in FIG. 2. Because only particular antigens have a structure matching the antigen binding sites of a particular antibody, that antibody will bind only that antigen, and no others. For example, an antibody against human serum albumin (HSA) will bind HSA in human serum, while ignoring the thousands of other proteins in the serum.

Antibodies can be created de novo against specific antigens using monoclonal antibody techniques in mice, for example. Using these techniques, researchers can obtain new antibodies against known antigens, which can then be used for research and assays, such as ELISA (defined below) and Western blotting. Additionally, thousands of different antibodies are readily available from a number of suppliers, such as Sigma Aldrich of St. Louis, Mo. A comprehensive list of antibody suppliers is available from Linscott's directory (http://www.linscottsdirectory.com/search/antibodies). Additionally, it is possible to raise antibodies against non-biological agents, such as chemical compounds derived from petroleum. For example, antibodies may be raised against melamine, which has been linked to contaminated infant formulas.

ELISA (Enzyme-Linked Immuno-Sorbent Assay) incorporates antibodies to detect specific chemical or biological species. In one method of ELISA, an unknown amount of antigen is affixed to a surface, and then a specific antibody (linked to an enzyme) is washed over the surface so that it can bind to the antigen. The surface is then washed with a buffer to remove any unbound antibodies.

By adding a chemical species that is converted to a fluorescent or colorimetric molecule by the enzyme, it is possible to infer the presence of antigens for which the known antibodies are specific. That is, bound antibody-enzyme complexes will fluoresce in the presence of light of the appropriate wavelength or otherwise be spectroscopically detectable. However, if no antibodies have bound, there will be no fluorescence or colorimetric change. By measuring the intensity of the fluorescence or color produced it is also possible to infer a relative amount of antigen present in the sample.

ELISA suffers from a number of limitations. It is time- and labor-intensive, requiring several preparation and wash steps, and quantitative measurements require the use of expensive light sources and detection equipment (e.g., a fluorimeter or spectrophotometer). However, the sensitivity and specificity of ELISA offsets these limitations. Because of the sensitivity and specificity, ELISA is commonly used to detect the presence of viruses, such as HIV, in human serum. ELISA is also commonly used in the food processing industry to screen for allergens, such as peanut or egg proteins or other contaminants such as chemicals or microorganisms. It is also known to employ parallel ELISA testing with multiple antibody solutions, e.g., using a 96 well microtiter plate.

The specificity and sensitivity of ELISAs are the consequence of using antibodies that have been chosen because of their specificity to the antigens that are being screened. Nonetheless, a lower-cost antibody-based sensor may allow for greater utilization of antibody detection. For example, massive parallel antibody screening would be very useful in the fields of genomics and proteomics.

Furthermore, if antibody-based sensors could be produced that were both portable and stable over long periods of time, such sensors could be deployed by homeland security agencies, allowing the agencies to quickly detect and characterize pathogens in the event of a suspected chemical or biological weapons attack.

SUMMARY

In one aspect, the invention may provide, among other things, a sensor comprising an electronic circuit electrically coupled to a type III-V semiconductor material and an antibody contacting the type III-V semiconductor material.

The electronic circuit of the sensor measures an electrical property of the type III-V semiconductor material. Electrical properties measurable by the electronic circuit may include resistivity (conductivity), capacitance, impedance, and inductance.

In another aspect, the invention may provide, among other things, a method of detecting an antigen comprising making a first measurement of an electrical property of a sensor comprising an antibody contacting a type III-V semiconductor material, contacting the sensor with an analyte that may or may not contain an antigen, and subsequently making a second measurement of the electrical property of the sensor comprising an antibody contacting a type III-V semiconductor material. Using this method, a difference between the first measurement and the second measurements indicates the presence of an antigen.

In another aspect, the invention may provide, among other things, a method of detecting a reaction of an analyte to a stimulus. The method comprises making a first measurement of an electrical property of a first sensor and a second sensor, wherein the first sensor and the second sensor comprise antibodies contacting a type III-V semiconductor material. The first sensor is contacted with an analyte that has not been exposed to the stimulus, while the second sensor is contacted with an analyte that has been exposed to the stimulus. Subsequently a second measurement of the electrical property of the first sensor and the second sensor is made. A difference between the first measurement and the second measurement for the first sensor or the second sensor indicates a response of the first sensor or the second sensor to the analyte. A difference between the response of the first sensor and the response of the second sensor indicates a reaction of the analyte to the stimulus.

In another aspect, the invention may provide, among other things, a method of making a sensor incorporating an antibody. The method comprises contacting a type III-V semiconductor material with an antibody and coupling a circuit capable of measuring an electrical property of the type III-V semiconductor material to the type III-V semiconductor material. Antibodies appropriate for use in the method include IgG, IgA, IgM, IgD, and IgE proteins.

In another aspect, the invention may provide, among other things, an electronic device comprising a type III-V semiconductor material having a modified surface and an antibody bound to the modified surface. Using an electronic circuit, an electrical property of the type III-V semiconductor material may be measured. Electrical properties measurable by the electronic circuit may include resistivity (conductivity), capacitance, impedance, and inductance. The surface of the type III-V semiconductor material may be modified by degreasing and wet-etching the surface of the type III-V semiconductor material. The electrical property of the type III-V semiconductor material with the antibody bound to the modified surface will change when the device is exposed to an antigen.

BRIEF DESCRIPTION OF THE DRAWINGS

As shown in FIG. 1, the IgG protein has three domains: two $F_{ab}$ domains with antigen binding sites at their ends, and one central $F_c$ domain that does not bind to antigens. One or more carboxylate groups near the end of the $F_c$ domain are capable of binding to type III-V semiconductor materials.

As shown in FIG. 11, the sensors of the invention can be reproducibly constructed with minimum deviations in normalized baseline measurements.

DETAILED DESCRIPTION

Figure 1:
FIG. 1 shows an immunoglobulin G protein (IgG) of the type used in an embodiment of the invention.
Figure 2:
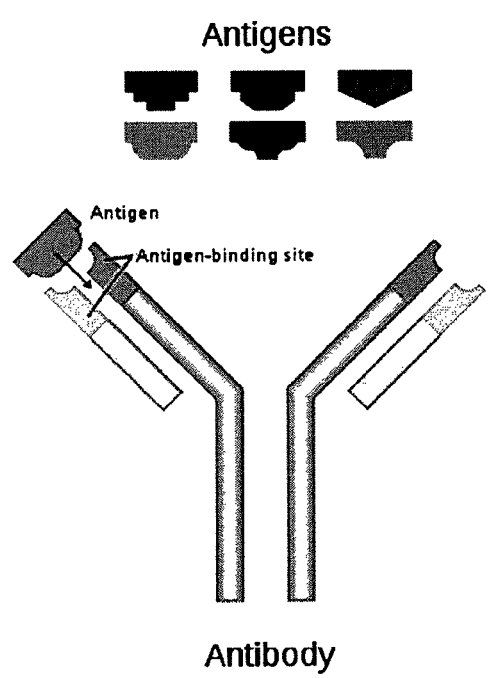
FIG. 2 illustrates the "lock and key" binding between an antibody and an antigen. Typically each antibody binds only to antigens having a specific stereochemical structure that compliments the antigen binding site of the antibody.

Before any embodiments of the invention are described in detail, it is to be understood that the invention is not limited in its application to the details of construction and the arrangement of components set forth in the following description. The invention is capable of other embodiments and of being practiced or of being carried out in various ways. Also it is to be understood that the phraseology and terminology used herein is for the purpose of description and should not be regarded as limiting. The use of "including," "comprising," or "having" and variations thereof herein is meant to encompass the items listed thereafter and equivalents thereof, as well as additional items. Unless specified or limited otherwise, the terms "mounted," "connected," "supported," and "coupled" and variations thereof encompass both direct and indirect mountings, connections, supports, and couplings. Further, "connected" and "coupled" are not restricted to physical or mechanical connections or couplings.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

Further, no admission is made that any reference, including any patent or patent document, cited in this specification constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinency of any of the documents cited herein.

A sensor comprising an antibody, a type III-V semiconductor material, and an electronic circuit is provided. Typically the antibody and electronic circuit are coupled to the type III-V semiconductor material such that the electronic circuit creates a signal when the antibody binds an antigen. The electronic circuit produces a signal because the binding of an antigen to the antibody connected to the type III-V semiconductor material causes a change in one or more electrical properties of the type III-V semiconductor material with connected antibody. The electrical property monitored by the circuit may include, but need not be limited to, resistance, capacitance, and inductance. Because the sensor employs antibodies, the sensor has a high affinity for certain antigens while producing no response in the presence of antigens having similar, but not identical, structures.

Sensors of the invention may become the basis for a sensor array capable of simultaneously identifying a host of antigens. Such an array may have tens, or hundreds, or thousands of sensors of the invention. The array may comprise redundant sensors for an antigen to reduce the risk of false positives and false negatives. The array may also comprise multiple different antigen sensors to enable the simultaneous identification of multiple antigens. Such antigens may include, but need not be limited to, viruses, pathogens, fungi, bacteria, prions, proteins, amino acids, nucleic acids, carbohydrates, hormones, chemical compounds, and chemical reaction intermediates. In particular, arrays made be constructed that are sensitive to chemical or biological warfare agents, such as ricin, anthrax, botulism toxin, or smallpox. These antigens may be found in a number of analytes, including, but not limited to bodily fluids of animals (e.g., blood, saliva, urine, mucus, sweat, tears) extracts of plants, industrial process streams, air, drinking water, and foodstuffs.

Figure 3:
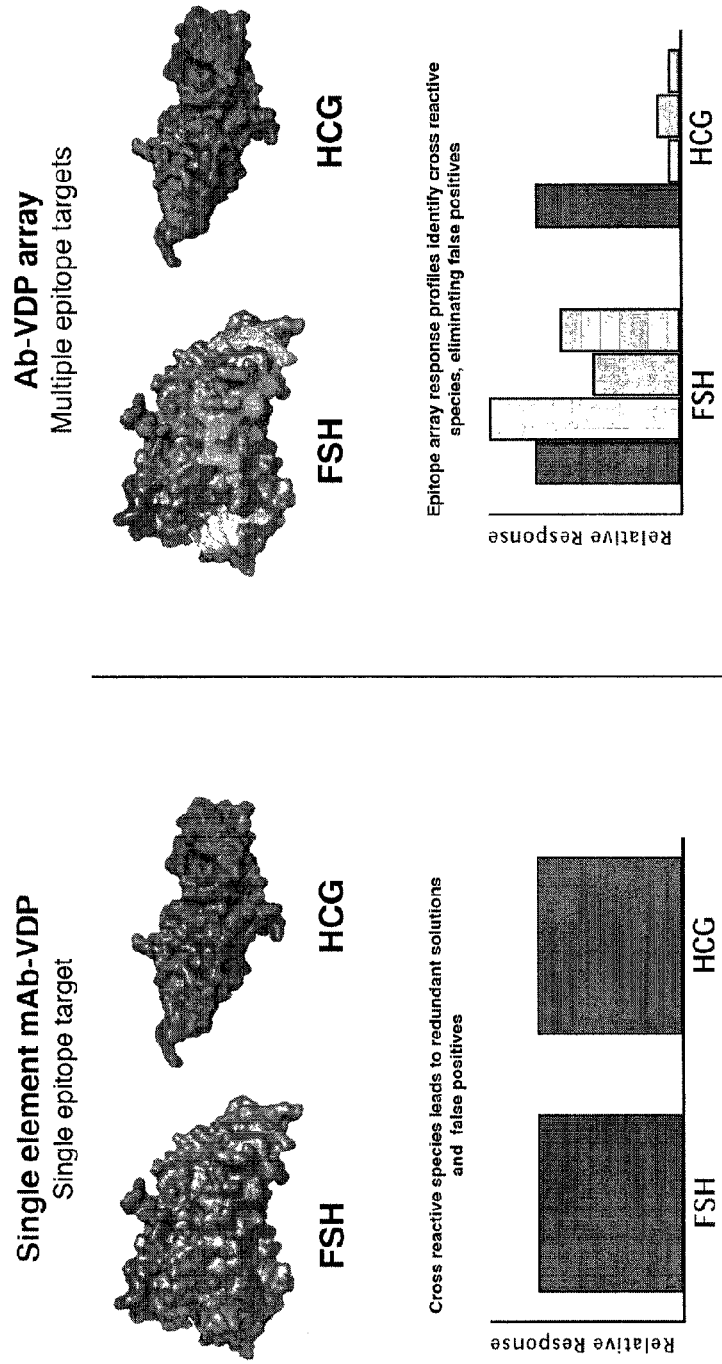
FIG. 3 illustrates that an antibody raised against an epitope of a particular antigen may also be sensitive to other antigens having the same or similar epitopes. By simultaneously observing multiple antibodies sensitive to different epitopes of the same antigen, the rate of false positives will be reduced.

Because of the tremendous variety in available antibodies, it is possible to inexpensively incorporate multiple different antibodies that are sensitive to the same antigen, or sensitive to a different binding region on the antigen. Thus, it is possible to build in redundancy not only by having multiples of the same antibodies, but by having multiples of different antibodies which bind to the targeted antigen. Such redundancies will dramatically reduce the rate of false positive identification. For example, as shown in FIG. 3, a monoclonal antibody raised against a single epitope of the target antigen will bind the same or similar epitopes present in non-target antigens. A sensor employing only this monoclonal antibody would identify both FSH and HCG proteins as being a match for FSH (FIG. 3 left). However, by incorporating multiple antibodies which bind to different epitopes of FSH, the sensor can easily distinguish between FSH and HCG (FIG. 3 right).

The method of making these sensors typically comprises preparing a portion of a type III-V semiconductor material, connecting the material to a circuit capable of measuring an electronic property of the type III-V semiconductor material and materials functionalized thereto, and then functionalizing the type III-V semiconductor material with antibodies. Typically the portion of type III-V semiconductor material is degreased, wet etched, and then exposed to a solution comprising antibodies raised against the antigen(s) of interest. The sensor then sits for a period with the solution comprising antibodies. The solution of antibodies is removed, the sensor is washed with an organic solvent and the sensor is dried with dry nitrogen.

Figure 4:
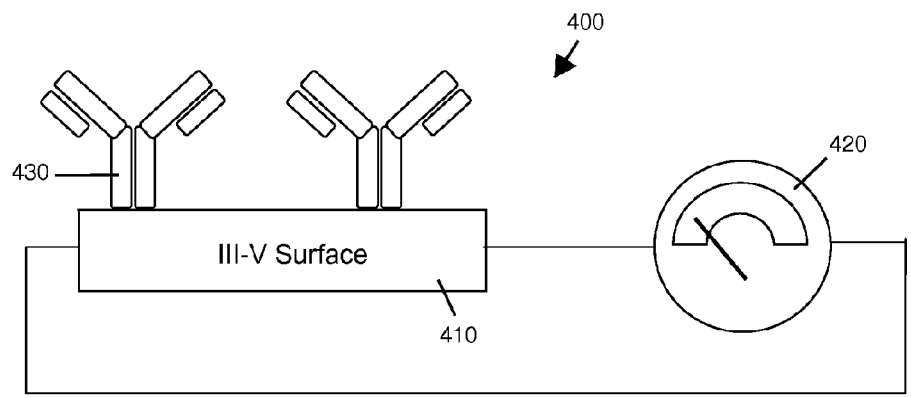
FIG. 4 is a graphical overview of an embodiment of the invention. In this simplified embodiment, a sensor comprises a type III-V semiconductor material functionalized with antibodies and a circuit capable of measuring an electrical property of the type III-V semiconductor material functionalized with antibodies. In the presence of an antigen to which the antibodies bind, the circuit measures a change in the electrical property that was measured prior to the introduction of the antigen. Thus, a change in an electrical property of the type III-V semiconductor material functionalized with antibodies is indicative of the presence of an antigen.
Figure 4:
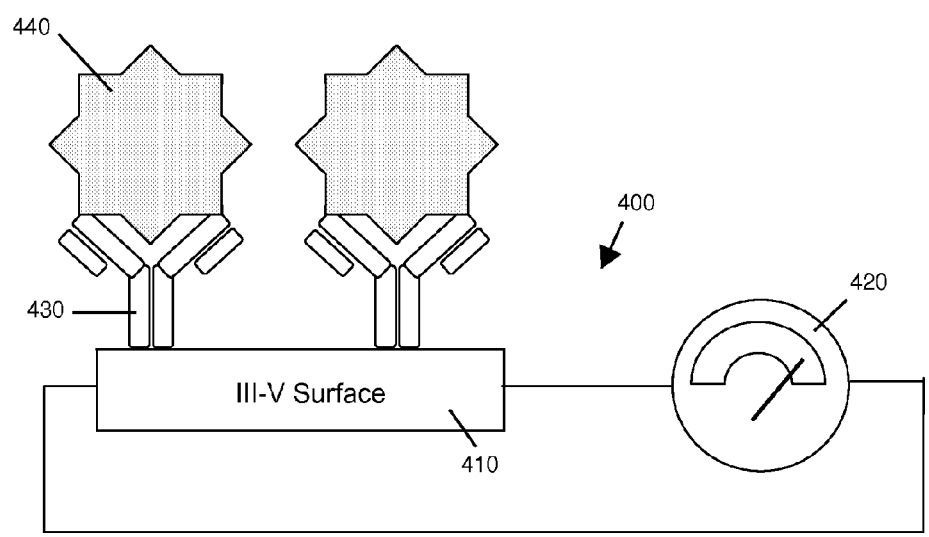

An overview diagram of an embodiment of a sensor 400 incorporating antibodies is shown in FIG. 4. Sensor 400 comprises type III-V semiconductor material 410, circuit 420, and antibodies 430. As shown in FIG. 4A, in the absence of an antigen 440 that binds to the antibodies of the sensor, the circuit displays a first value (baseline) of an electrical property of the sensor. As shown in FIG. 4B, in the presence of antigen 440 to which the antibodies bind, the circuit measures a second value of the electrical property that was measured prior to the introduction of the antigen. Thus, a change in an electrical property of the type III-V semiconductor material functionalized with antibodies is indicative of the presence of an antigen.

The sensors of the invention typically comprise a type III-V semiconductor material that is suitably prepared to receive one or more antibodies. Type III-V semiconductors suitable for the invention include, but need not be limited to, indium arsenide (InAs), gallium arsenide (GaAs), gallium nitride (GaN), and indium nitride (InN). Without being limited by any theory, type III-V semiconductor materials are favorable for use in sensors of the present invention because type III-V semiconductor materials are capable of bonding to carboxylate moieties after the type III-V semiconductor materials are degreased and wet-etched.

Prior to functionalizing the surface, the semiconductor material is typically connected to an electronic circuit capable of measuring one or more electrical properties of the semiconductor material and materials functionalized to the semiconductor material. Such properties may include, but need not be limited to, resistivity, conductivity, inductance, impedance, and capacitance. For example, the resistivity of a semiconductor material and materials functionalized to the semiconductor material may be measured by attaching four contacts to the portion of type III-V semiconductor material and monitoring the electrical potential between two contacts as a steady current is fed between the remaining two contacts. Other methods of measuring resistivity (or conductance) may be used.

The capacitance of a semiconductor material and materials functionalized to the semiconductor material may likewise be measured by attaching an electrode to opposite sides of the semiconductor material and then monitoring for changes in the capacitance with a capacitance meter. Other methods for monitoring for changes in capacitance, such as the observation of the decay of an RC circuit, with the semiconductor material acting as the capacitor may be used.

The inductance of a semiconductor material and materials functionalized to the semiconductor material may also be measured by attaching an electrode to opposite sides of the semiconductor material and then monitoring for changes in the inductance with an inductance meter. Other methods for monitoring for changes in inductance, such as the observation of the decay of an LC circuit, with the semiconductor material acting as the inductor, are known to those of skill in the art.

A circuit suitable for the measurement of an electrical property of a semiconductor material and materials functionalized to the semiconductor material may be purchased from a number of known suppliers, such as Agilent (Palo Alto, Calif.), Tektronix (Richardson, Tex.), or Fluke (Everett, Wash.). Additionally, suitable circuits can be produced using card edge test equipment and software, such as that sold by National Instruments (Austin, Tex.). Multiplexed measurements, such as those necessary for evaluating arrays of sensors, may require specialized fabrication, however such methods are within the purview of the artisan of ordinary skill.

In preparation for functionalizing the type III-V semiconductor materials with antibodies, type III-V semiconductor materials may be degreased with acetone, or other suitable organic solvents including, but not limited to ketones, mineral spirits, or naphthas. Type III-V semiconductor materials may be wet etched with hydrofluoric acid diluted in a solvent, including but not limited to, methanol, ethanol, and isopropanol.

After degreasing and wet etching, it is possible to functionalize the type III-V semiconductor materials by simply exposing the material to aqueous solutions comprising antibodies. Because a large variety of antibodies are commercially available, a large variety of sensors can be inexpensively produced. Commercial producers of antibodies include Sigma Aldrich (St. Louis, Mo.), EMD Biosciences (San Diego, Calif.), Abnova, Inc. (Walnut, Calif.), Invitrogen (Carlsbad, Calif.), and Abcam (Cambridge, Mass.). Natural antibodies may be directly harvested from a number of organisms, or the antibodies may be created and harvested using known monoclonal antibody techniques. Antibody solutions suitable for use in the invention are greater than about 1 nM antibody in buffer, typically greater than about 100 nM antibody in buffer, more typically greater than about 1 µM antibody in buffer. The prepared surfaces are exposed to the antibody solutions for greater than about 1 hour, typically greater than about six hours, more typically greater than about 12 hours. In some embodiments, it may be beneficial to gently agitate the prepared surfaces while the aqueous solutions comprising antibodies is allowed to contact the prepared surfaces. A laboratory orbital shaker, or other similar device, may be used to agitate the prepared surfaces while they are contacted with the aqueous solutions comprising antibodies.

Figure 5:
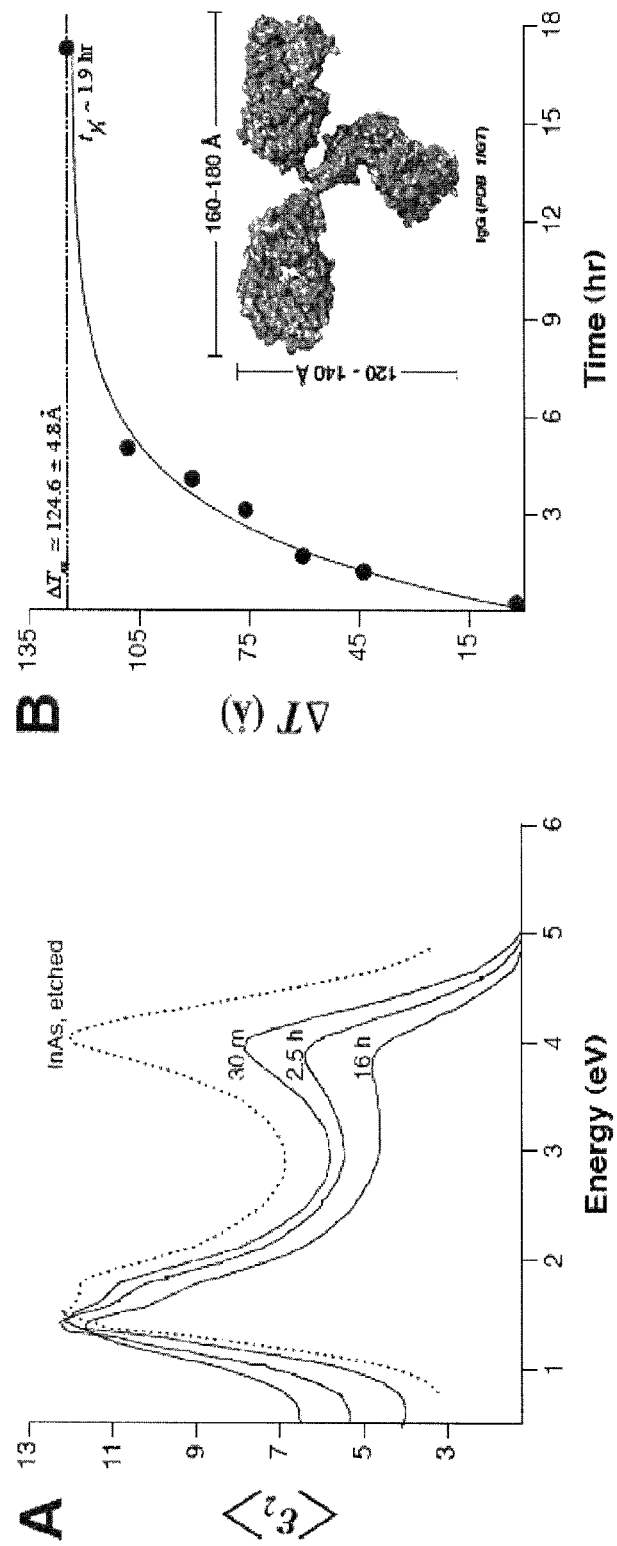
FIG. 5 shows surface ellipsometry data indicating the buildup of a layer of anti-HSA antibodies on a wet-etched InAs surface. After approximately sixteen hours, the wet-etched InAs surface forms a complete monolayer of anti-HSA antibodies. Repeated rinsing with PBS buffer and a chloroform/hexane mixture does not diminish the integrity of the anti-HSA antibody monolayer on the InAs surface.

Using surface ellipsometry (SE), it is possible to observe the real-time attachment of antibodies to prepared type III-V semiconductor materials. For example, SE can be used to quantify changes in the surface thickness of a layer of anti-HSA IgG deposited on a degreased and wet-etched InAs sample. As shown in left graph of FIG. 5, a SE peak at approximately 4 eV decreases with time as the anti-HSA IgG solution is allowed to react with the prepared InAs surface. The decrease in the peak at 4 eV correlates to a thickening of a layer of anti-HSA IgG on the InAs surface. Converting the SE data to length values, as shown in the right graph of FIG. 5, the thickness of anti-HSA IgG layer is observed to asymptotically approach 125 Å, which corresponds to the estimated long axis of IgG. This, in conjunction with the 1st-order kinetics of the reaction, suggests the InAs surface is functionalized with a single monolayer of IgG.

As a further test of the stability of the IgG monolayer, the remnant antibody solution can be removed from the functionalized surface, the functionalized surface rinsed with organic solvents, and completely dried with nitrogen. When the functionalized surface is rewetted with a buffer not containing antibodies, SE measurements still indicate a 125 Å layer on the surface. It is expected that the sensors can be stored in a dried state for some time without degradation of the antibody surface functionality.

In one embodiment, a sensor incorporating an antibody is constructed upon an indium arsenide (InAs) material connected to an electronic circuit. The circuit may be arranged in a van der Pauw configuration to measure changes in sheet resistivity that result from the antibodies selectively binding antigens. The methods of making an indium arsenide-based sensor in a van der Pauw configuration are described in U.S. Provisional patent applications No. 61/129,274 filed Jun. 16, 2008 and No. 61/136,072 filed Aug. 11, 2008, both of which are incorporated herein in their entireties. The methods of making aluminum gallium arsenide- and gallium arsenide-based sensor in van der Pauw configurations are additionally described in U.S. Provisional patent applications No. 61/129,273 filed Jun. 16, 2008 and No. 61/136,073 filed Aug. 11, 2008, both of which are incorporated herein in their entireties. Additional relevant methods of preparing materials and making sensors are disclosed in WO 2010/005738, incorporated herein by reference in its entirety.

In some sensors using van der Pauw configurations, a current is applied across a first edge of the type III-V semiconductor material and the voltage is measured at a second edge on the opposite side of the sample. Typically the process is then repeated with a different set of edges and applied current direction. For example, a current can be applied across the second edge (or another edge) while a voltage measurement is made on a different (e.g., the first) edge. The resulting voltage measurements may be used to determine the sheet resistivity of the type III-V semiconductor material or the type III-V semiconductor material functionalized with antibodies. As is known in the art, a square van der Pauw sensor would have two sets of opposing edges and measurements may be taken from both sets of edges. The results of the multiple measurements may be averaged to yield a value for the sheet resistivity of the type III-V semiconductor material or the type III-V semiconductor material functionalized with antibodies.

Figure 6:
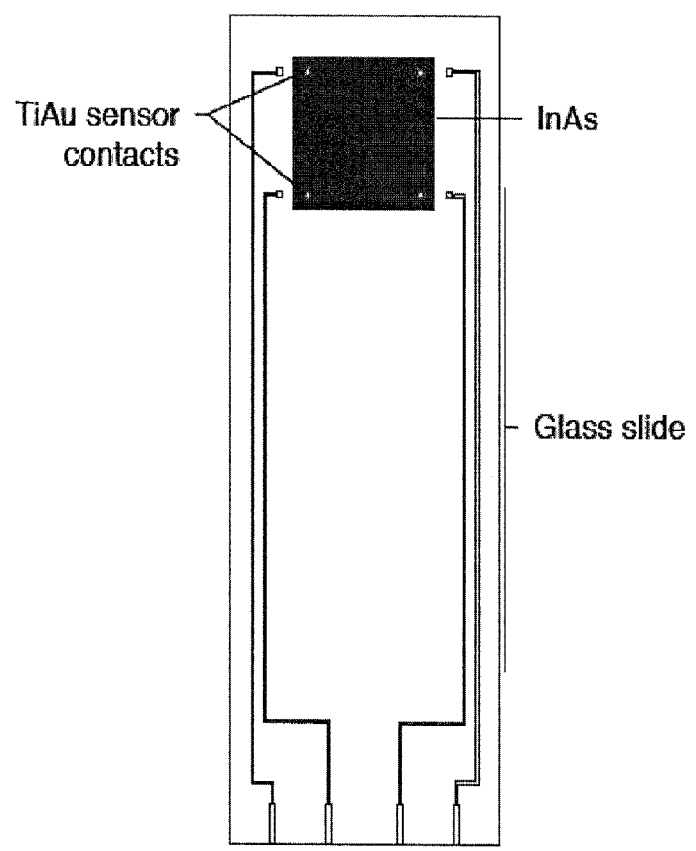
FIG. 6 shows a sensor precursor comprising a glass slide, a 1 cm×1 cm square of InAs foil, metallized contacts, and Ti/Au sensor contacts. The sensor will ultimately detect the presence of antigen binding by monitoring the sheet resistance of the InAs square in the completed sensor (see FIG. 7).

In one embodiment, a square piece of type III-V semiconductor film is secured on a glass slide with metallized contacts, as shown in FIG. 6. Semiconductor films are available from a number of suppliers including IQE, Inc. (Bethlehem, Pa.). The metallized contacts may be connected to the type III-V film with gold wires, for example. The type III-V film may also be connected to exterior circuitry with push pins and probe cards designed to receive sensor films. Other methods for producing exterior connections to the type III-V film may be achieved with known techniques of lithography, e.g., ion beam lithography and photolithography.

Figure 7:
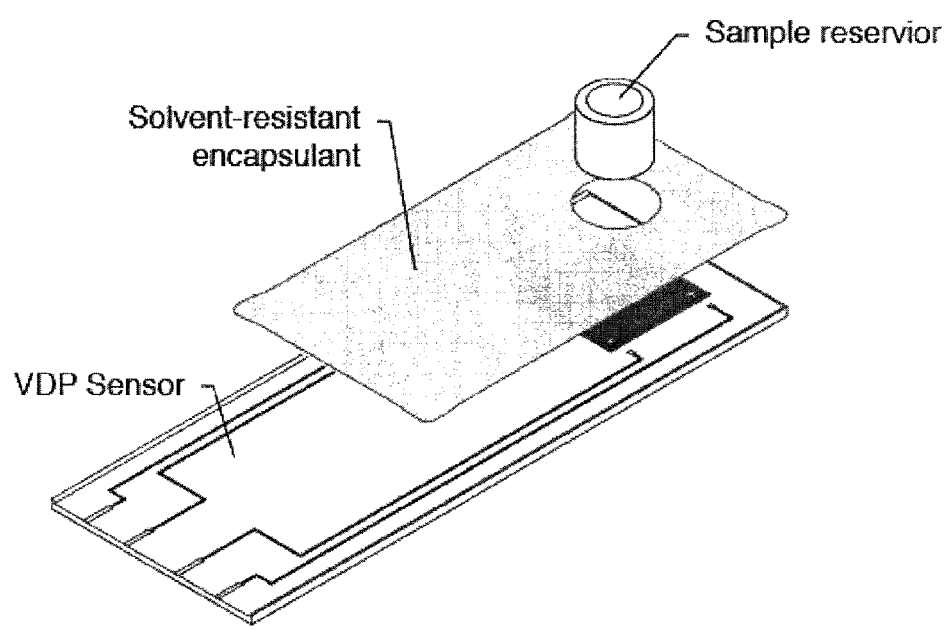
FIG. 7 shows assembly of the remaining components of a sensor, prior to final preparation of the InAs surface and exposure to an antibody solution. A 1 cm long by 1 cm O.D. segment of quartz tubing is fused to the InAs surface with solvent resistant epoxy. The portion of the InAs foil outside of the segment of quartz tubing, the metallized contacts and the Ti/Au sensor contacts are also covered in solvent resistant epoxy.

In one embodiment, a well for holding the antibody solutions during the growth may be constructed from a segment of quartz tubing, such as is available from National Scientific (Quakertown, Pa.). The tube is connected to the type III-V surface with a solvent resistant adhesive such as a resin or epoxy, and the contacts and gold wires covered with a protective coating of solvent resistant resin or epoxy, as is shown in FIG. 7. Once the structure of FIG. 7 is complete, the type III-V surface can be degreased, wet-etched, and exposed to antibody solutions to make a sensor of the invention.

In another aspect, the invention may provide, among other things, a method of detecting antigens comprising contacting an antigen with a sensor of the invention. Because of the known diversity of antibodies, sensors of the invention may make it possible to detect millions of different antigens, including but not limited to, viruses, pathogens, fungi, bacteria, prions, proteins, amino acids, nucleic acids, carbohydrates, hormones, chemical compounds, and chemical reaction intermediates. Because massive parallel measurements of these antigens are possible with arrays based upon sensors of the invention, the invention provides a valuable tool for various bioinformatics techniques such as genomics and proteomics.

Typically, an antigen is detected by first taking a background measurement of an electrical property of the sensor after exposing the sensor to a buffered aqueous sample lacking antigen (e.g., PBS buffer). Next, an aqueous sample of interest (e.g., suspected of containing antigen) is allowed to contact a sensor of the invention for a period of several hours, the aqueous sample of interest is removed, the sensor conditioned (e.g., with a mixture of chloroform and hexane) and the electrical property of the sensor remeasured. A variation in the value of the electrical property may be indicative of the presence of the antigen.

Prior to using sensors of the invention for the detection of an antigen, a baseline is typically measured for the sensor by exposing the sensor to the buffer that will be used to detect the presence of an antigen. Buffers appropriate for use with the invention may include, but need not be limited to, phosphate buffered saline (PBS), Tris-HCl, Tris-Bis propane, HEPES, and MOPS. The buffers are typically buffered to physiological pHs, e.g., approximately 7.4. Suitable buffers are available from Sigma-Aldrich, for example. Typically the buffer is allowed to interact with the sensor for some time, the buffer washed away, the sensor cleaned with a chloroform/hexane mixture, and the sensor dried with nitrogen. An electrical property of the sensor is then measured to establish the baseline for the electrical property. The chloroform/hexane mixture suitably comprises greater than about 1% chloroform, typically greater than about 2% chloroform, more typically greater than about 5% chloroform.

After establishing the baseline, the sensor is exposed to a sample containing an antigen that has been diluted in the same buffer. The samples are diluted at least 1:1 with buffer, typically at least 1:10 with buffer, more typically at least 1:20 with buffer. The buffer containing the antigen is allowed to contact the sensor for some time. In some embodiments, it may be beneficial to gently agitate the sensor while the buffer containing the antigen is allowed to contact the sensor. A laboratory orbital shaker, or other similar device may be used to agitate the sensor while it is contacted with the antigen. The sensors are exposed to the antibody solutions for greater than about 15 minutes, typically greater than about one hour, more typically greater than about 4 hours.

After the buffer containing the antigen has been allowed to contact the sensor for some time, the antigen and buffer are removed, the sensor rinsed with a chloroform/hexane mixture, and the sensor dried with nitrogen. Once dried, an electronic property of the type III-V material with functionalized antibodies can be measured. A marked difference in the value of the electronic property is indicative that the sample contained an antigen specific to an antibody incorporated into the invention. The presence of an antigen will cause at least about a 0.5% variation in the value of the measured electrical property, typically at least about a 1% variation in the value of the measured electrical property, more typically at least about a 2% variation in the value of the measured electrical property.

The arrangement of a sensor of the invention need not be limited to the arrangement shown in FIG. 7, however. For example, any suitable solvent-resistant material may be used to construct a reservoir on the type III-V material in order to allow for the exposure of the type III-V to antibody solutions. Such solvent resistant material may include specialty epoxies and plastics that are resistant to the chemical treatments used in the invention. It is additionally possible that type III-V may be deposited on an appropriate material using known evaporative deposition technology.

The sensors of the invention may be scaled down so that hundreds, or thousands, of sensors can be fit on a material to make an array of sensors. For example, using known lithographic techniques and evaporative deposition, it may be possible to create a 12×12 array of InAs patches each with four contacts sufficiently insulated from each other to allow independent sheet resistivity measurements of each InAs patch. A 12×12 array of protective material may then be bonded to the material to create a 12×12 array of reservoirs suitable for degreasing and wet-etching the InAs material in preparation for receiving antibody solutions. After the InAs material has been prepared, 144 different antibodies can be distributed into the 144 separate wells using known microfluidic techniques. After an appropriate reaction time, the 144 wells may be aspirated, washed with solvents, and dried to make an array of antibody sensors. Such an array would be dramatically less expensive to operate than other chemical array sensors. It is also conceivable that such arrays may be incorporated into a handheld device to allow mobile detection of antigens.

The devices and methods of the invention are not limited to detecting the presence of antigens in an analyte. The devices and methods of the invention may also be used to measure a response of an analyte to a stimulus. As is known to those of skill in the art, a stimulus will produce a cascade of events in many biological systems. In many instances, the cascade results in the production of chemical or biological species that will bind to antibodies specific for those species. Such stimuli include, but need not be limited to allergens, metabolic targets (e.g., carbohydrates, lipids, peptides), microorganisms, electromagnetic or particle radiation, pharmaceuticals, and environmental hazards (e.g., chemicals and heavy metals). Additional electrical or thermal components may additionally be added to the sensors to measure non-chemical/biological stimuli. Non-chemical biological/stimuli include, but need not be limited to temperature, electric fields, and magnetic fields.

Figure 8:
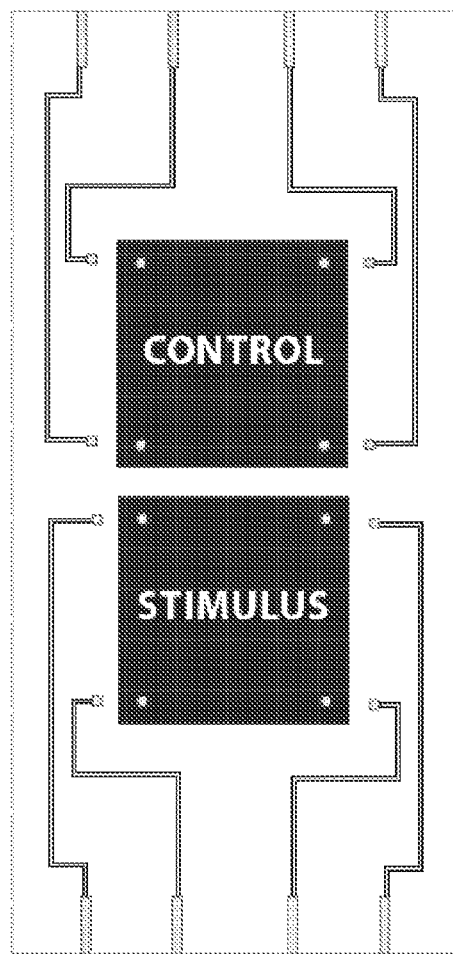
FIG. 8 shows a dual sensor embodiment useful for measuring the response of an analyte to a stimulus. Reservoirs (as described below) are not shown for the sake of clarity.
Figure 9:
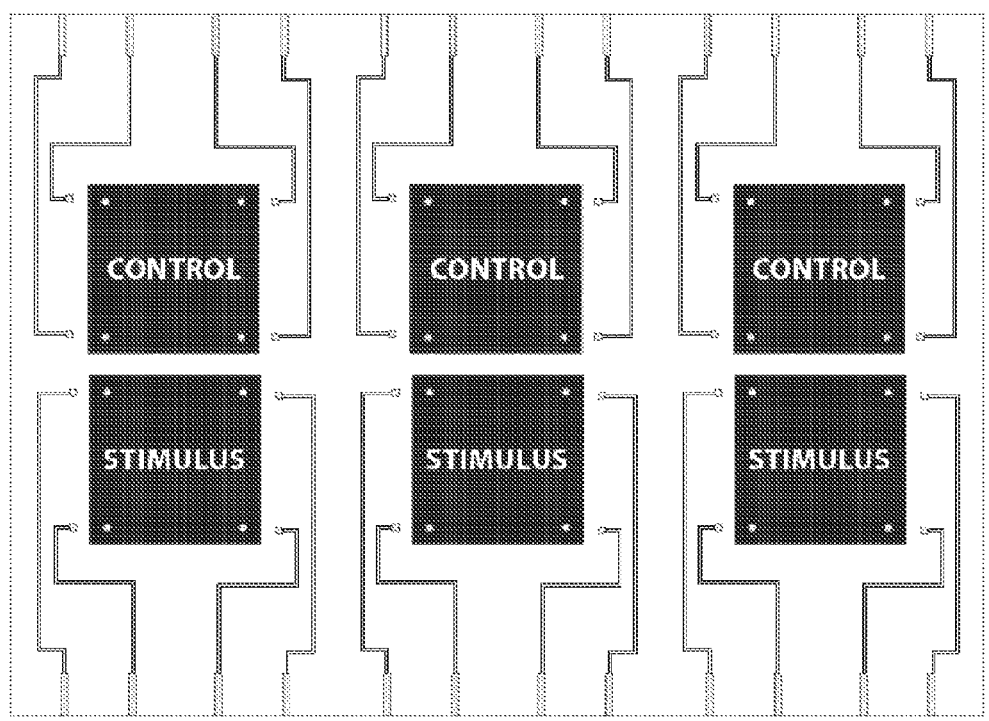
FIG. 9 shows a six-sensor embodiment useful for simultaneously measuring the response of an analyte to multiple stimuli. The reservoirs are not shown for the sake of clarity.

Because of the simplicity of the devices of the invention, it is possible to inexpensively construct duplicate sensors, one being a control and the other being exposed to one or more stimuli. For example, a stimulus sensor incorporating two antibody sensors, as shown in FIG. 8, is readily constructed using the techniques described herein. (The sensors in FIG. 8 do not include the reservoirs for clarity.) An electrical property of the two antibody sensors may be simultaneously measured prior to exposure to an analyte, and after exposure to an analyte. The response of the analyte to the stimuli is easily assessed by not exposing the control side to the stimuli while exposing the stimulus side to the stimuli and holding all other variables constant. With little effort, the dual sensor may be expanded to multiple sensors, as shown in FIG. 9. This may allow one analyte to be simultaneously tested for a response to multiple stimuli.

Figure 10:
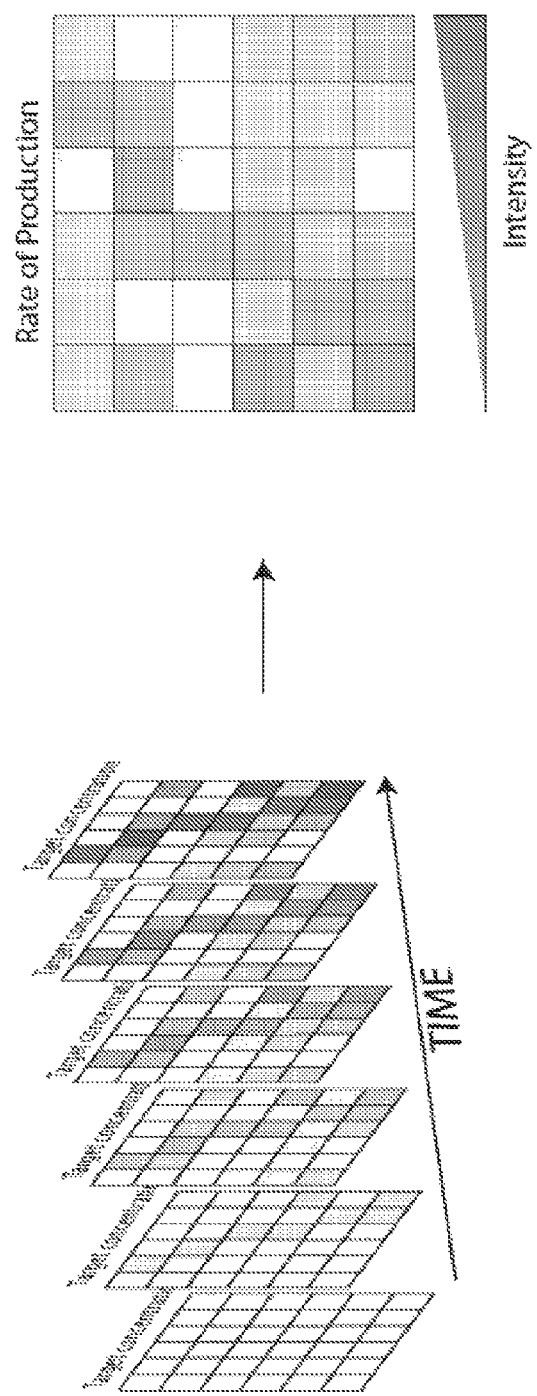
FIG. 10 shows an array of sensors incorporating antibodies which may be used to determine the response of an analyte to a gradient of stimuli.

In advanced embodiments, an array of sensors may be constructed, as is illustrated in FIG. 10. A concentration gradient of stimuli may be used to establish response curves or to make chemical equilibrium measurements. Additional electrical or thermal components may additionally be added to the sensor to create other gradients, such as temperature gradients. In other embodiments, the time of exposure of the analyte to the stimulus may be varied in order to determine rates curves.

The following examples are illustrative and are not to be construed as limiting the scope of the invention.

EXAMPLES

Example 1—Indium Arsenide (InAs), Anti-Human Serum Albumin (Anti-HSA) IgG-Based Sensor A reservoir-slide structure was fabricated as follows: A 1 cm×1 cm square of InAs film (IQE, Inc.) was mounted with double sided tape (3M, St. Paul, Minn.) on a glass slide (Fisher Scientific, Waltham, Mass.) having electrical contacts bonded to the surface. (See, e.g., FIG. 6.) Gold wire (SurePure Chemetals, Florham Park, N.J.) was bonded between the electrical connections and the four corners of the InAs square with a solvent resistant epoxy (Resinlab EP1785, Resinlab, Germantown, Wis.). The resulting arrangement will allow for measurements of sheet resistivity of the InAs square using a van der Pauw method.

The connections between the InAs square and the electrical connectors were confirmed with a voltmeter (Fluke, Everett, Wash.). After electrical continuity was verified, a 1 cm long×1 cm O.D. piece of quartz tubing (National Scientific, Quakertown, Pa.) was mounted perpendicularly to the InAs square in the center of the InAs square, thus creating a reservoir. The quartz was sealed to the InAs with a solvent-resistant epoxy. Additional solvent-resistant epoxy was next applied to the exposed electrical contacts on the glass slide, gold wire bonds between the slide and InAs square, and the portions of the InAs surface lying outside the quartz reservoir. (See, e.g., FIG. 7.) After the epoxy was applied, the reservoir-slide structure was allowed to cure for 48 hours in ambient air.

The InAs inside the quartz reservoir were degreased by filling the reservoir with acetone, allowing the acetone to sit for five minutes, and then emptying out the acetone. A five-minute rinse was then done with methanol. The InAs inside the reservoir was then wet etched for two minutes with 100 mM hydrofluoric acid in methanol. The etching solution was drained, and the reservoir was rinsed with methanol. Immediately after the methanol was removed, the reservoir was filled with a 1:10 distilled water dilution of an anti-HSA IgG solution (Sigma-Aldrich, St. Louis, Mo.). The quartz reservoir was covered with Parafilm and allowed to sit for ten hours. After ten hours, the reservoir was aspirated, rinsed with a solution of 5% (v/v) solution of chloroform in hexane, re-aspirated, and then dried with dry nitrogen. The reservoir of the finished HSA sensor was covered with Parafilm for storage.

Example 2—Stability of HSA Sensor

The Parafilm was removed from the reservoir of the HSA sensor of Example 1, and the reservoir was equilibrated with 200 µL of phosphate buffered saline (PBS buffer) (pH 7.4, Sigma Aldrich). The HSA sensor was allowed to sit for 30 minutes, and then the PBS buffer was aspirated from the reservoir. The reservoir was rinsed with a solution of 5% (v/v) solution of chloroform in hexane, re-aspirated, and then dried with dry nitrogen. The HSA sensor of Example 1 was connected to a 20 channel multiplexer/source meter (Keithley Instruments, Cleveland, Ohio) via a 20 pin card edge connector (CW Industries, Southampton, Pa.). Software modules used for remote operation of the source meter, data acquisition, and off-line analysis were prepared using LabView software (National Instruments, Austin, Tex.).

To establish a baseline sheet resistance for the HSA sensor, a series of voltage measurements were taken at current values between 20 µA-3 mA. After the first set of measurements were completed, the reservoir was filled with PBS buffer, the buffer was allowed to sit for 30 minutes, the buffer was aspirated from the reservoir, the reservoir rinsed with a solution of 5% (v/v) solution of chloroform in hexane, re-aspirated, and then the reservoir was dried with dry nitrogen. The sheet resistivity measurements were then repeated. The reservoir was refilled with buffer, allowed to sit for 30 minutes, emptied, rinsed with the chloroform/hexane solution, and dried with nitrogen two additional times to produce a set of four measurements.

The percent standard deviation of the four sheet resistance values after the reservoir was exposed to PBS buffer was <0.5%.

Figure 11:
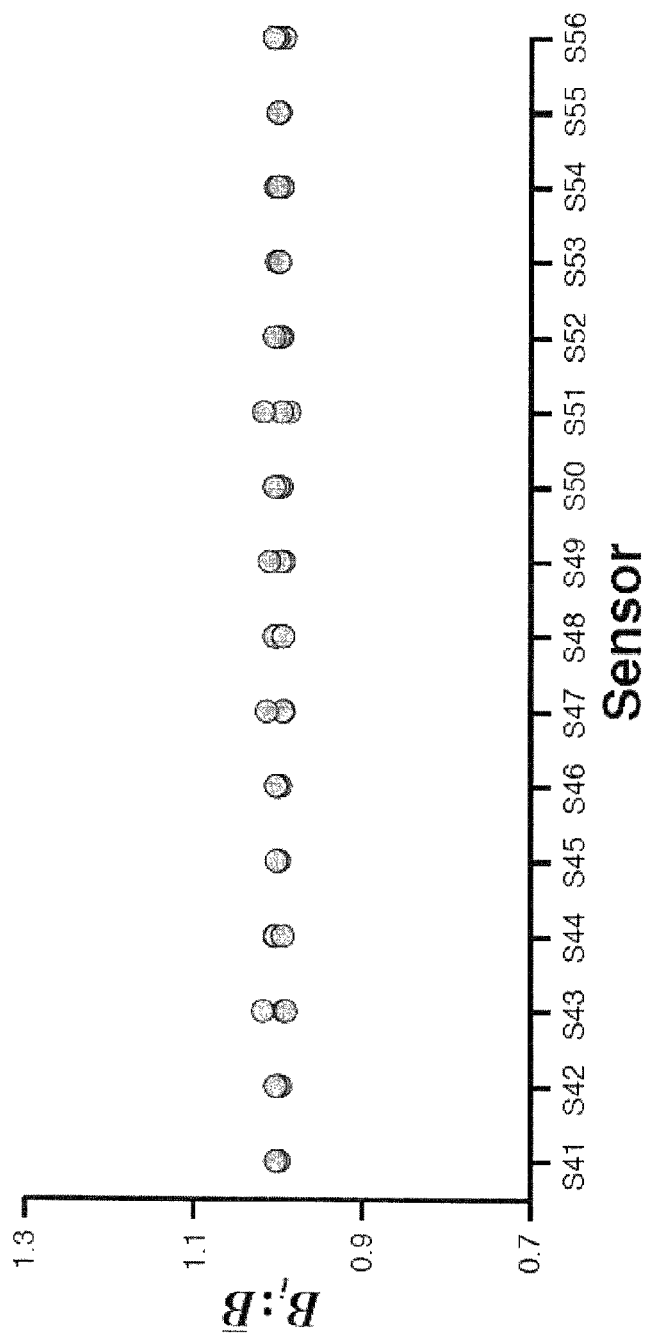
FIG. 11 shows a series of baseline measurements on fifteen identically-constructed HSA sensors.

As an additional demonstration of the stability of the fabrication techniques, fifteen HSA sensors were prepared according to the techniques of Example 1. All of sensors were then exposed to PBS buffer for 30 minutes, the reservoirs emptied, rinsed with the chloroform/hexane solution, and dried with nitrogen. The sheet resistivity of each HSA sensor was measured four times by averaging voltage measurements across two sides of the InAs square as a current was applied to the opposing sides. The four measured sheet resistivities of each sensor were averaged, and then each individual measurement was normalized against the average $$\frac{B_i}{B}$$

to produce the graph shown in FIG. 11. As can be seen from FIG. 11, there was little variation in the normalized sheet resistivity of the fifteen sensors (less than 0.4%).

Example 3—Detection of HSA with HSA Sensor

A purified HSA solution (Sigma Aldrich) was serially diluted with PBS buffer to 1:16000 and filtered. The baseline for the HSA sensor of Example 2 was measured after the HSA sensor was exposed to PBS buffer without HSA. Next, 200 µL of the diluted HSA solution in PBS was pipetted into the reservoir, the reservoir covered with Parafilm, and the sensor was allowed to sit, holding the HSA solution, for 15 hours. After 15 hours, the HSA solution was aspirated away, the reservoir rinsed with the chloroform/hexane mixture as above, and dried with dry nitrogen. A series of voltage measurements were taken at current values between 20 µA-3 mA to establish a sheet resistivity. The absolute relative change in sheet resistance, defined as $$\sqrt{\frac{(R_{avg} - R)^2}{R_{avg}}},$$

wherein R is the sheet resistance of the HSA sensor after being exposed to HAS, and $R_{avg}$ is the average sheet resistance from the initial baseline measurements, was 1.2±0.3.

Example 4—Selectivity of HSA Sensor for HSA Over HCG

Two new HSA sensors were prepared according to Example 1. A baseline value was measured for both of the new HSA sensors according to Example 2. After measuring baseline values, one HSA sensor was loaded with 200 µL of a 1:16000 dilution of HSA in PBS buffer (pH 7.4). The second HSA sensor was loaded with 200 µL of a 1:16000 dilution of human chorionic gonadotropin (HCG) in PBS buffer (pH 7.4). The HSA sensors were covered with Parafilm and allowed to sit for 15 hours. After 15 hours, HSA/HCG solutions were aspirated away, the reservoirs washed with the chloroform/hexane mixture as above, and dried with dry nitrogen. Sheet resistance measurements were then made on both HSA sensors. The absolute relative change in sheet resistance of the HSA sensor that had been exposed to HSA was 1.2±0.3. The absolute relative change in sheet resistance of the HSA sensor that had been exposed to HCG was 0.06±0.03. Thus, the HSA sensor was approximately 20 times more sensitive to HSA than HCG.

Example 5—Construction of TNFα Sensor

A reservoir-slide structure was fabricated as follows: A 1 cm×1 cm square of InAs film (American Elements, Los Angeles, Calif.) was mounted with double sided tape (3M, St. Paul, Minn.) on a glass slide (Fisher Scientific, Waltham, Mass.) having electrical contacts bonded to the surface. (See, e.g., FIG. 6.) Gold wire (SurePure Chemetals, Florham Park, N.J.) was bonded between the electrical connections and the four corners of the InAs square with a solvent resistant epoxy (Resinlab EP1785, Resinlab, Germantown, Wis.). The resulting arrangement will allow for measurements of sheet resistivity of the InAs square using a van der Pauw method.

The connections between the InAs square and the electrical connectors were confirmed with a voltmeter (Fluke, Everett, Wash.). After electrical continuity was verified, a 1 cm long×1 cm O.D. piece of quartz tubing (National Scientific, Quakertown, Pa.) was mounted perpendicularly to the InAs square in the center of the InAs square, thus creating a reservoir. The quartz was sealed to the InAs with a solvent-resistant epoxy. Additional solvent-resistant epoxy was next applied to the exposed electrical contacts on the glass slide, gold wire bonds between the slide and InAs square, and the portions of the InAs surface lying outside the quartz reservoir. (See, e.g., FIG. 7.) After the epoxy was applied, the reservoir-slide structure was allowed to cure for 48 hours in ambient air.

The InAs inside the quartz reservoir was degreased by filling the reservoir with acetone, allowing the acetone to sit for five minutes, and then emptying out the acetone. A five-minute rinse was then done with methanol. The InAs inside the reservoir was then wet etched for two minutes with 100 mM hydrofluoric acid in methanol. The etching solution was drained, and the reservoir was rinsed with methanol. Immediately after the methanol was removed, the reservoir was filled with a 1:10 distilled water dilution of an anti-TNFα IgG solution (Abcam). The quartz reservoir was covered with Parafilm and allowed to sit for ten hours. After ten hours, the reservoir was aspirated, rinsed with a solution of 5% (v/v) solution of chloroform in hexane, re-aspirated, and then dried with dry nitrogen. The reservoir of the finished TNF sensor was covered with Parafilm for storage.

Example 6—Construction of an IL 1β Sensor

A reservoir-slide structure was fabricated as follows: A 1 cm×1 cm square of InAs film (American Elements, Los Angeles, Calif.) was mounted with double sided tape (3M, St. Paul, Minn.) on a glass slide (Fisher Scientific, Waltham, Mass.) having electrical contacts bonded to the surface. (See, e.g., FIG. 6.) Gold wire (Surepure Chemetals, Florham Park, N.J.) was bonded between the electrical connections and the four corners of the InAs square with a solvent resistant epoxy (Resinlab EP1785, Resinlab, Germantown, Wis.). The resulting arrangement will allow for measurements of sheet resistivity of the InAs square using a van der Pauw method.

The connections between the InAs square and the electrical connectors were confirmed with a voltmeter (Fluke, Everett, Wash.). After electrical continuity was verified, a 1 cm long×1 cm O.D. piece of quartz tubing (National Scientific, Quakertown, Pa.) was mounted perpendicularly to the InAs square in the center of the InAs square, thus creating a reservoir. The quartz was sealed to the InAs with a solvent-resistant epoxy. Additional solvent-resistant epoxy was next applied to the exposed electrical contacts on the glass slide, gold wire bonds between the slide and InAs square, and the portions of the InAs surface lying outside the quartz reservoir. (See, e.g., FIG. 7.) After the epoxy was applied, the reservoir-slide structure was allowed to cure for 48 hours in ambient air.

The InAs inside the quartz reservoir was degreased by filling the reservoir with acetone, allowing the acetone to sit for five minutes, and then emptying out the acetone. A five-minute rinse was then done with methanol. The InAs inside the reservoir was then wet etched for two minutes with 100 mM hydrofluoric acid in methanol. The etching solution was drained, and the reservoir was rinsed with methanol. Immediately after the methanol was removed, the reservoir was filled with a 1:10 distilled water dilution of an anti-IL 1 β IgG solution (Abcam). The quartz reservoir was covered with Parafilm and allowed to sit for ten hours. After ten hours, the reservoir was aspirated, rinsed with a solution of 5% (v/v) solution of chloroform in hexane, re-aspirated, and then dried with dry nitrogen. The reservoir of the finished IL 1 β sensor was covered with Parafilm for storage.

Example 7—Construction of an Interleukin 6 (IL 6) Sensor

A reservoir-slide structure was fabricated as follows: A 1 cm×1 cm square of InAs film (American Elements, Los Angeles, Calif.) was mounted with double sided tape (3M, St. Paul, Minn.) on a glass slide (Fisher Scientific, Waltham, Mass.) having electrical contacts bonded to the surface. (See, e.g., FIG. 6.) Gold wire (Surepure Chemetals, Florham Park, N.J.) was bonded between the electrical connections and the four corners of the InAs square with a solvent resistant epoxy (Resinlab EP1785, Resinlab, Germantown, Wis.). The resulting arrangement will allow for measurements of sheet resistivity of the InAs square using a van der Pauw method.

The connections between the InAs square and the electrical connectors were confirmed with a voltmeter (Fluke, Everett, Wash.). After electrical continuity was verified, a 1 cm long×1 cm O.D. piece of quartz tubing (National Scientific, Quakertown, Pa.) was mounted perpendicularly to the InAs square in the center of the InAs square, thus creating a reservoir. The quartz was sealed to the InAs with a solvent-resistant epoxy. Additional solvent-resistant epoxy was next applied to the exposed electrical contacts on the glass slide, gold wire bonds between the slide and InAs square, and the portions of the InAs surface lying outside the quartz reservoir. (See, e.g., FIG. 7.) After the epoxy was applied, the reservoir-slide structure was allowed to cure for 48 hours in ambient air.

The InAs inside the quartz reservoir was degreased by filling the reservoir with acetone, allowing the acetone to sit for five minutes, and then emptying out the acetone. A five-minute rinse was then done with methanol. The InAs inside the reservoir was then wet etched for two minutes with 100 mM hydrofluoric acid in methanol. The etching solution was drained, and the reservoir was rinsed with methanol. Immediately after the methanol was removed, the reservoir was filled with a 1:10 distilled water dilution of an anti-IL 6 IgG solution (Sigma-Aldrich, St. Louis, Mo.). The quartz reservoir was covered with Parafilm and allowed to sit for ten hours. After ten hours, the reservoir was aspirated, rinsed with a solution of 5% (v/v) solution of chloroform in hexane, re-aspirated, and then dried with dry nitrogen. The reservoir of the finished IL 6 sensor was covered with Parafilm for storage.

Example 8—Comparison of Sensitivity and Selectivity of TNF, IL 1β, and HSA Sensors Comparing sheet resistivities between sensors constructed with different antibodies may be meaningless in some cases. For example, a sensor constructed with anti-HSA IgG has a markedly different baseline sheet resistivity than a sensor constructed with anti-IL 1β. Even when the HSA sensor has been exposed to HSA, the sheet resistivity is still greater than the baseline sheet resistivity for an IL 1 β sensor. For this reason, it is beneficial to normalize the measured resistivity of a given sensor after exposure to an antigen against the baseline sensor resistivity after exposure to buffer. The specificity, β, of a particular antibody sensor to an antigen can be defined as $$\beta_{antigen} = \frac{R_{baseline} - R_{antigen}}{R_{baseline}}$$

Figure 12:
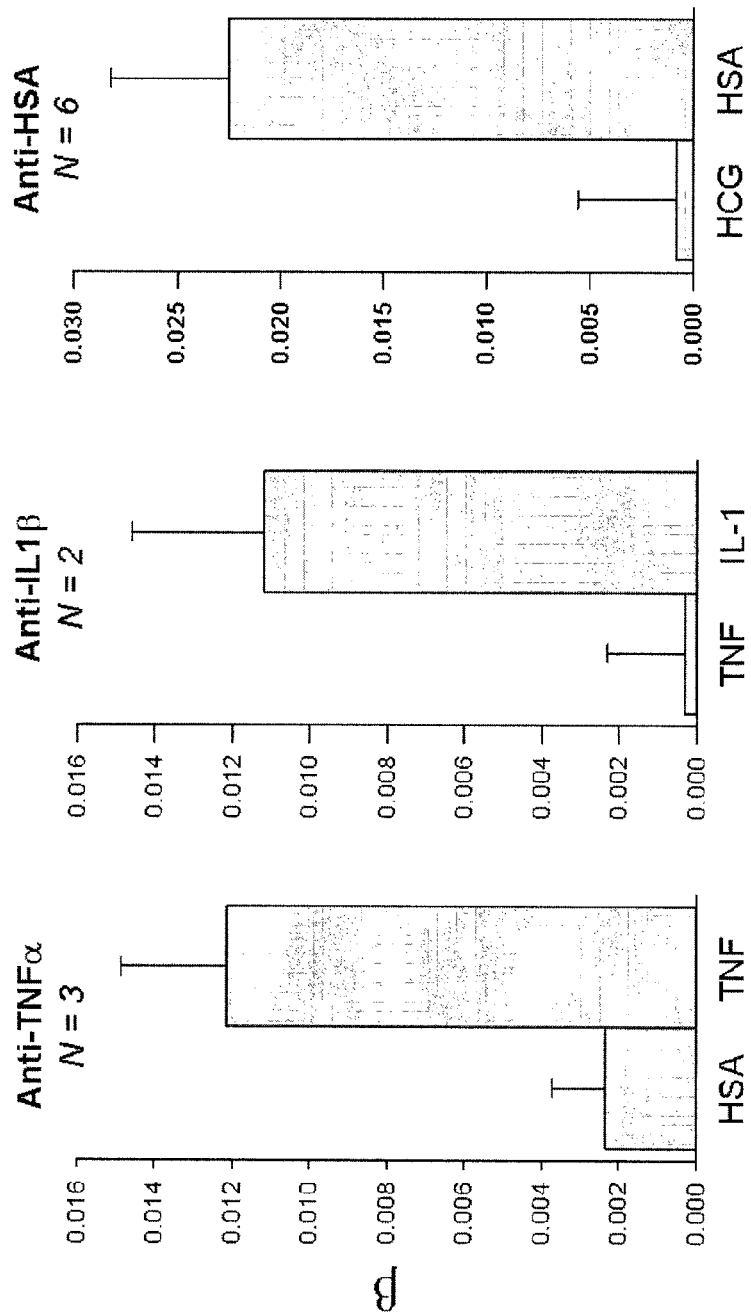
FIG. 12 shows specific binding of three different types of sensors. Three tumor necrosis factor (TNF) sensors showed an average six-fold higher sensitivity to TNF over human serum albumin (HSA). Two Interleukin 1β (IL 1β) sensors showed a thirty fold higher sensitivity to IL 1β over TNF. Six HSA sensors showed an average one hundred-fold higher sensitivity to HSA over human chronic gonadotropin (HCG).
Figure 13:
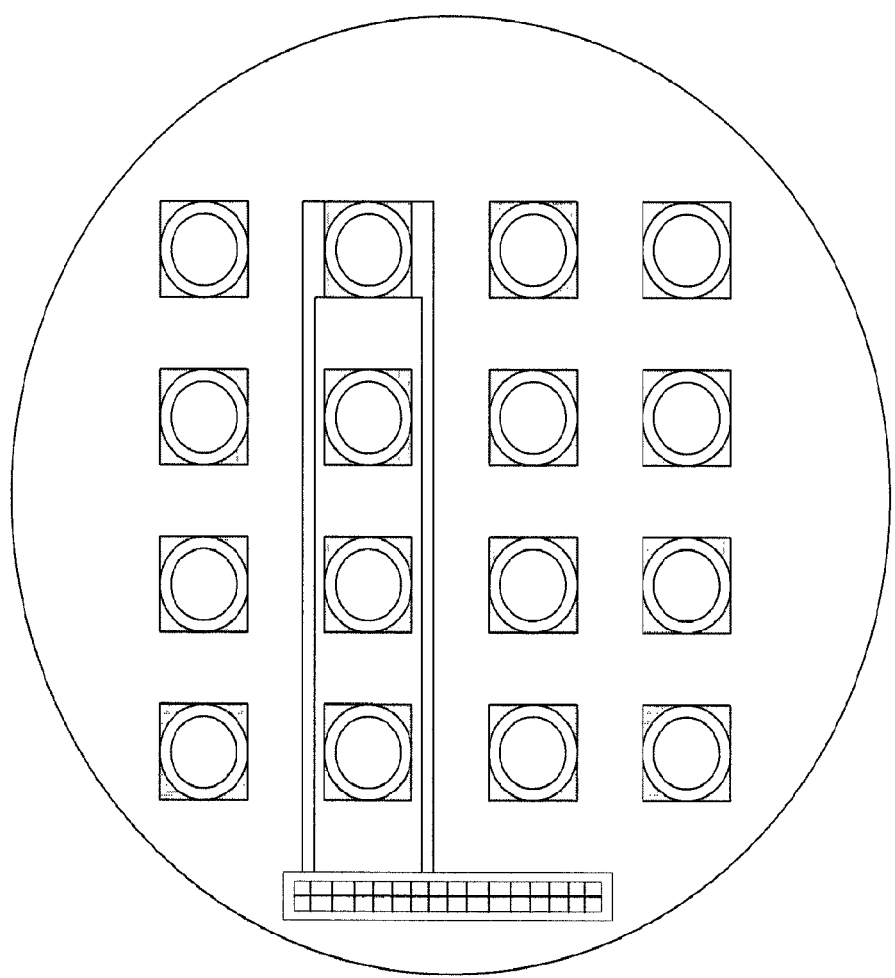
FIG. 13 illustrates a sensor comprising an array of reservoirs, each reservoir capable of being functionalized with a different antibody. In one embodiment of this configuration all of the reservoirs will have antibodies specific to different antigens. In another embodiment, the sensor may be prepared with duplicative antibodies to increase redundancy to reduce false negatives. In another embodiment, the sensor may be prepared with different antibodies that bind to different epitopes of the same antigen to reduce false positives.

FIG. 12 compares $\beta_{antigen}$ for TNF sensors of Example 5, IL 1β sensors of Example 6, and HSA antibody sensors of Example 1. Three tumor necrosis factor (TNF) sensors showed an average six-fold higher sensitivity to TNF over human serum albumin (HSA). Two Interleukin 1β(IL 1β) sensors showed a thirty fold higher sensitivity to IL 1β over TNF. Six HSA sensors showed an average one hundred-fold higher sensitivity to HSA over human chronic gonadotropin (HCG).

Thus, as is shown in FIG. 12, the methods of the invention are capable of producing sensors with an order of magnitude more specificity for specific proteins than for similar proteins that are not specific to the antibodies used in the sensor.

PROPHETIC EXAMPLES

Example 9—Construction of a Dual Sensor Incorporating Anti-Interferon γ Antibodies A mycobacterial protein (such as ESAT-6) response sensor may be used to verify a patient's exposure to *Mycobacterium tuberculosis*, the organism responsible for human Tuberculosis. A dual sensor comprising anti-interferon γ antibodies will be constructed as follows: Similar to the structure of FIG. 8, two 1 cm×1 cm squares of InAs film (American Elements, Los Angeles, Calif.) will be mounted with double sided tape (3M, St. Paul, Minn.) on a glass slide (Fisher Scientific, Waltham, Mass.) having electrical contacts bonded to the surface. (See, e.g., FIG. 8.) Gold wires (Surepure Chemetals, Florham Park, N.J.) will be bonded between the electrical connections and the four corners of each InAs square with a solvent resistant epoxy (Resinlab EP1785, Resinlab, Germantown, Wis.). The resulting arrangement will allow for measurements of sheet resistivity of each InAs square using a van der Pauw method.

The connections between the InAs square and the electrical connectors will be confirmed with a voltmeter (Fluke, Everett, Wash.). After electrical continuity is verified, a 1 cm long×1 cm O.D. piece of quartz tubing (National Scientific, Quakertown, Pa.) will be mounted perpendicularly to each InAs square in the center of each InAs square, thus creating a reservoir. The quartz will be sealed to the InAs with a solvent-resistant epoxy. Additional solvent-resistant epoxy will be applied to the exposed electrical contacts on the glass slide, gold wire bonds between the slide and the InAs squares, and the portions of the InAs surfaces lying outside the quartz reservoir. (That is, similar to the arrangement of FIG. 7, but having two InAs squares as shown in FIG. 8.) After the epoxy is applied, the reservoir-slide structures will be allowed to cure for 48 hours in ambient air.

The InAs inside the quartz reservoirs will be degreased by filling the reservoirs with acetone, allowing the acetone to sit for five minutes, and then emptying out the acetone. A five-minute rinse will then be done with methanol. The InAs inside the reservoir will then be wet etched for two minutes with 100 mM hydrofluoric acid in methanol. The etching solution will be drained, and the reservoir will be rinsed with methanol. Immediately after the methanol is removed, the reservoir will be filled with a 1:10 distilled water dilution of an anti-interferon γ antibody solution (Sigma-Aldrich, St. Louis, Mo.). The quartz reservoirs will be covered with Parafilm and allowed to sit for ten hours. After ten hours, the reservoirs will be aspirated, rinsed with a solution of 5% (v/v) solution of chloroform in hexane, re-aspirated, and then dried with dry nitrogen. The reservoirs of the finished anti-interferon γ sensors will be covered with Parafilm for storage.

Example 10—Test for Exposure to *Mycobacterium Tuberculosis*

A sample of human blood from a subject exposed to *Mycobacterium tuberculosis* will be tested for its response to ESAT-6 as follows: A baseline sheet resistance measurement will be made for the dual sensor comprising anti-interferon γ antibodies described in Example 9. A series of voltage measurements will be taken at current values between 20 μA-3 mA for each of the sensors. After baseline sheet measurements of each sensor are completed, the blood sample will be diluted 100-fold with PBS buffer, and 200 μL of this diluted sample will be placed in each of the reservoirs of the dual sensor of Example 9.

One of the sensors (hereafter "control") will be covered with Parafilm. The other sensor (hereafter "stimulus") will have an additional 50 μL of a 1 μM solution of ESAT-6 in PBS buffer added, and then the stimulus sensor will be covered with Parafilm. The dual sensor comprising anti-interferon γ antibodies will be left to agitate gently on a laboratory orbital shaker for 15 hours. After 15 hours, the blood samples will be aspirated away, the reservoirs washed with a chloroform/hexane mixture, and dried with dry nitrogen. Sheet resistance measurements will then be made on both sensors. The sheet resistance of both sensors will be normalized against the baseline sheet resistance measurements to achieve response readings. The stimulus sensor will show at least a 10-fold greater response than the control sensor because prior exposure of the subject to *Mycobacterium tuberculosis* results in an increased production of interferon γ upon exposure to ESAT-6.

Example 11—Sensor Having an Array of Antibodies

Using photolithography, a 4×4 array of 1 cm×1 cm indium arsenide (InAs) squares will be deposited on a 2" radius silicon wafer, with an intervening insulation layer between the silicon surface and the InAs. Using photolithography, 64 electrical contacts will be created, one contact going to each of the four corners of each of the 16 InAs squares. The 64 contacts will be arranged so that each of the contacts terminates in a central location on the silicon wafer. A 64-pin connector will be soldered to the central location such that each contact will correspond to a separate pin on the connector.

Sixteen 1 cm long×1 cm O.D. pieces of quartz tubing will be mounted perpendicularly to the InAs squares, thus creating 16 reservoirs. The quartz will be sealed to the InAs with a solvent-resistant epoxy. Additional solvent-resistant epoxy will be applied to the exposed electrical contacts on the silicon wafer, and the portions of the InAs surface lying outside the quartz reservoir. After the epoxy is applied, the reservoir-slide structure will be allowed to cure for 48 hours in ambient air. The final assembled sensor will resemble FIG. 13.

The InAs inside the 16 quartz reservoirs will be degreased by filling the reservoirs with acetone, allowing the acetone to sit for five minutes, and then emptying out the acetone. A five-minute rinse will be done with methanol. The InAs inside the reservoir will be wet etched for two minutes with 100 mM hydrofluoric acid in methanol. The etching solution will be drained, and the reservoir will be rinsed with methanol. Immediately after the methanol is removed, each of the reservoirs will be filled with a 1:10 distilled water dilution of one of four different antibody solutions (Sigma-Aldrich, St. Louis, Mo.). The resultant sensor will, thus, have two sensors incorporating each antibody. The sensor having an array of antibodies will be covered with Parafilm and allowed to sit for ten hours. After ten hours, the reservoirs will be aspirated, rinsed with a solution of 5% (v/v) solution of chloroform in hexane, re-aspirated, and then dried with dry nitrogen. Each of the 16 reservoirs will then be filled with buffer, and the sheet resistance of each of the 16 sensors will be measured several times in order to establish a baseline for each sensor.

The resulting sensor having an array of antibodies will be challenged with a prepared solution comprising a mixture of the four antigens against which the antibodies of the sensor have been raised. After removing the buffer solutions and rinsing each reservoir with the chloroform/hexane solution, four of the reservoirs (one of each type of antibody) will be filled with the prepared solution. The remaining four reservoirs (one of each type of antibody) will be filled with a solution containing only the antigen against which the antibody was raised. The sensor having an array of antibodies will be covered with Parafilm and allowed to sit for 15 hours. After 15 hours, the solutions will be aspirated away, the reservoirs will be washed with the chloroform/hexane mixture, and will be dried with dry nitrogen. Sheet resistance measurements will then made on all reservoirs of the sensor. The data will show that the sensor having an array of antibodies correctly identified the presence of the four antigens in the solution comprising a mixture of the four antigens against which the antibodies of the sensor have been raised. Furthermore, the sensor having an array of antibodies will show the same level of sensitivity to the solutions containing only the individual antigens.

All patents, publications and references cited herein are hereby fully incorporated by reference. In case of conflict between the present disclosure and incorporated patents, publications and references, the present disclosure should control.

Thus, the invention provides, among other things, a sensor incorporating antibodies, as well as methods of using and making a sensor incorporating antibodies. Various features and advantages of the invention are set forth in the following claims.

The invention claimed is:

1. A sensor comprising:
a type III-V semiconductor material having a first edge and a second edge,
an antibody contacting the type III-V semiconductor material, and
an electronic circuit electrically coupled to the type III-V semiconductor material,
the first edge of the type III-V semiconductor material configured for applying current to said first edge and the second edge configured for measuring voltage at said second edge to determine a first value of an electrical property of the semiconductor material, wherein the electronic circuit measures the electrical properly of the type III-V semiconductor material,
such that when an antigen binds to the antibody, the electrical property has a second value different from the first value.

2. The sensor of claim 1, wherein the antibody comprises at least one of an IgG protein, an IgA protein, an IgM protein, an IgD protein, and an IgE protein.

3. The sensor of claim 1, wherein the antibody binds an antigen selected from the group consisting of Tumor Necrosis Factor (TNF), Human Serum Albumin (HSA), Interleukin 1β (IL 1β), Interleukin 6 (IL 6), Follicle Stimulating Hormone (FSH), Interferon γ, or Human Chorionic Gonadotropin (HCG), and combinations thereof.

4. The sensor of claim 3, wherein the antibody comprises at least one of an IgG protein, an IgA protein, an IgM protein, an IgD protein, and an IgE protein.

5. The sensor of claim 1, wherein the antigen is selected from a prion, a protein, an amino acid, a nucleic acid, a carbohydrate, a hormone, a chemical compound, a chemical reaction intermediate, or a combination thereof.

6. The sensor of claim 5, wherein the antibody comprises at least one of an IgG protein, an IgA protein, an IgM protein, an IgD protein, and an IgE protein.

7. The sensor of claim 1 having a van der Pauw configuration.

8. The sensor of claim 1, further comprising a reservoir positioned to receive an analyte therein and contact the analyte with the type III-V material.

9. The sensor of claim 1, wherein the electrical property is resistivity.

10. The sensor of claim 9, wherein resistivity is sheet resistivity.

11. The sensor of claim 1, wherein the type III-V semiconductor material comprises at least one of indium arsenide (InAs), gallium arsenide (GaAs), gallium nitride (GaN), indium nitride (InN) and a combination thereof.

12. The sensor of claim 1, further comprising an additional antibody, the antibody binding a first antigen, the additional antibody binding a second antigen.

13. The sensor of claim 1, further comprising a well.

14. A sensor array comprising a plurality of sensors of claim 1.

15. The sensor array of claim 14, comprising greater than ten sensors.

16. The sensor array of claim 14, comprising at least two different antibodies.

* * * * *